US006867269B2

(12) United States Patent
Sakamoto et al.

(10) Patent No.: US 6,867,269 B2
(45) Date of Patent: Mar. 15, 2005

(54) WATER-ABSORBENT RESIN AND PRODUCTION PROCESS THEREFOR

(75) Inventors: Shigeru Sakamoto, Himeji (JP); Yorimichi Dairoku, Himeji (JP); Yasuhiro Fujita, Himeji (JP); Yoshio Irie, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/472,048

(22) PCT Filed: Dec. 17, 2002

(86) PCT No.: PCT/JP02/13159

§ 371 (c)(1),
(2), (4) Date: Sep. 17, 2003

(87) PCT Pub. No.: WO03/051415

PCT Pub. Date: Jun. 26, 2003

(65) Prior Publication Data

US 2004/0110897 A1 Jun. 10, 2004

(30) Foreign Application Priority Data

Dec. 19, 2001 (JP) ........................................ 2001-386490

(51) Int. Cl.$^7$ ........................ C08F 220/06; A61L 15/60
(52) U.S. Cl. ........................... 526/73; 524/916; 526/63; 526/68; 526/70; 526/88; 526/317.1
(58) Field of Search ............................. 526/63, 68, 70, 526/73, 88, 317.1; 524/916

(56) References Cited

U.S. PATENT DOCUMENTS

| | | | |
|---|---|---|---|
| 4,552,938 A | | 11/1985 | Mikita et al. |
| 4,625,001 A | * | 11/1986 | Tsubakimoto et al. ........ 526/88 |
| 4,654,393 A | | 3/1987 | Mikita et al. |
| 4,703,067 A | | 10/1987 | Mikita et al. |
| 4,914,170 A | | 4/1990 | Chang et al. |
| 4,957,984 A | | 9/1990 | Itoh et al. |
| 4,985,518 A | | 1/1991 | Alexander et al. |
| 5,086,133 A | | 2/1992 | Itoh et al. |
| 5,185,413 A | | 2/1993 | Yoshinaga et al. |
| 5,380,808 A | | 1/1995 | Sumiya et al. |
| 5,385,983 A | * | 1/1995 | Graham .................... 525/330.1 |
| 5,399,591 A | * | 3/1995 | Smith et al. ................. 521/53 |
| 5,633,329 A | | 5/1997 | Hahnle et al. |
| 6,100,305 A | | 8/2000 | Miyake et al. |
| 6,140,395 A | | 10/2000 | Hatsuda et al. |
| 6,174,978 B1 | | 1/2001 | Hatsuda et al. |
| 6,187,828 B1 | | 2/2001 | Woodrum et al. |
| 6,657,015 B1 | * | 12/2003 | Riegel et al. ............. 525/329.9 |

FOREIGN PATENT DOCUMENTS

| | | | | |
|---|---|---|---|---|
| DE | 3831261 A1 | 3/1990 | | |
| EP | 0 280 541 A2 | 8/1988 | | |
| EP | 280541 A | * 8/1988 | ........... A61L/15/00 |
| EP | 0 347 241 A2 | 12/1989 | | |
| JP | 55-58208 | 4/1980 | | |
| JP | 55-147512 | 11/1980 | | |
| JP | 56-147809 | 11/1981 | | |
| JP | 58-71907 | 4/1983 | | |
| JP | 59-18712 | 1/1984 | | |
| JP | 63-275607 | 11/1988 | | |
| JP | 63-275608 | 11/1988 | | |
| JP | 1-165610 | 6/1989 | | |
| JP | 1-318022 | 12/1989 | | |
| JP | 2-129207 | 5/1990 | | |
| JP | 2-215801 | 8/1990 | | |
| JP | 4-175319 | 6/1992 | | |
| JP | 9-67404 | 3/1997 | | |
| JP | 10-45812 | 2/1998 | | |
| JP | 10-119042 | 5/1998 | | |
| JP | 10-182750 | 7/1998 | | |
| JP | 11-181005 | 7/1999 | | |
| JP | 11-188725 | 7/1999 | | |
| JP | 11188725 A | * 7/1999 | ........... B29B/13/10 |
| JP | 11-188726 | 7/1999 | | |
| JP | 11-188727 | 7/1999 | | |
| JP | 11-228604 | 8/1999 | | |
| WO | WO 01/38402 A1 | 5/2001 | | |
| WO | WO 200138402 A1 | * 5/2001 | ............ B01J/14/00 |
| WO | WO 03/022896 A1 | 3/2003 | | |

OTHER PUBLICATIONS

"An Efficient Preparation Method for Superabsorbent Polymers", CHEN, Journal of Applied Polymer Science, vol. 74, pp. 119–124 (1999).
Chemical Engineering Handbook, 6$^{th}$ Edition, edited by Society of Chemical Engineers, published by Marzun Co., Ltd. 1999, p. 843, Table 16.4 and English translation thereof.

* cited by examiner

Primary Examiner—Kelechi C. Egwim
(74) Attorney, Agent, or Firm—Roylance, Abrams, Berdo & Goodman, L.L.P.

(57) ABSTRACT

The present invention provides such a production process that a low-cost water-absorbent resin having excellent quality can be obtained by reasonable steps in aqueous solution polymerization. The production process for a water-absorbent resin comprises a polymerization setup that includes the steps of: supplying an aqueous solution of a water-soluble unsaturated monomer component including a major proportion of acrylic acid and/or its salt into a polymerization vessel causing shearing action; and then carrying out polymerization, involving crosslinking, of the water-soluble unsaturated monomer and at the same time carrying out fine division of the resultant hydrogel; with the production process being characterized in that the aqueous solution of the water-soluble unsaturated monomer component as supplied into the polymerization vessel has a temperature of not lower than 40° C.

21 Claims, No Drawings

US 6,867,269 B2

WATER-ABSORBENT RESIN AND PRODUCTION PROCESS THEREFOR

TECHNICAL FIELD

The present invention relates to: a water-absorbent resin, which is favorably used for various uses, such as sanitary articles (e.g. disposable diapers and sanitary napkins) and water-retaining agents for soil; and a production process therefor.

BACKGROUND ART

In recent years, water-absorbent resins are widely utilized for various uses, such as sanitary articles (e.g. disposable diapers, sanitary napkins, and incontinent articles for adult) and water-retaining agents for soil, and are mass-produced and consumed.

Particularly, in uses of sanitary articles such as disposable diapers, sanitary napkins, and incontinent articles for adult, the amount of the water-absorbent resins as used tends to increase, and the amount of a pulp fiber as used tends to decrease, in order to thin the resultant articles. The water-absorbent resins are desired to have large absorption capacity under a load. On the one hand, desired are low-cost water-absorbent resins because the amount of the water-absorbent resins as used per sheet of sanitary articles is large. Therefore, it is desired that: the energy consumption and the amount of discharged materials are decreased in production lines of water-absorbent resins, and thereby a reasonable production process is established.

In order to decrease costs for improving a ratio of performance of the water-absorbent resins to their costs, various attempts (e.g. a method which involves carrying out polymerization in a high monomer concentration; and a polymerization method which involves initiating polymerization in high temperature, evaporating water by heat of polymerization or heating, and obtaining a dried water-absorbent resin at a stroke) have hitherto been made as a method for carrying out aqueous solution polymerization of a monomer component that is converted to water-absorbent resins by the polymerization.

In gazettes of JP-A-071907/1983 (Arakawa Chemical Industries. Ltd.) and JP-A-018712/1984 (Arakawa Chemical Industries. Ltd.), disclosed is a method which involves polymerizing an aqueous acrylate salt solution having a high concentration of higher than 55 weight %, and obtaining a dried solid water-absorbent resin at a stroke. In a specification of U.S. Pat. No. 4,985,518 (American Colloid), disclosed is a method which involves polymerizing an aqueous acrylate salt solution having a high concentration of higher than 30 weight %, and obtaining a dried solid water-absorbent resin at a stroke. In a gazette of JP-A-058208/1980 (Kitani), disclosed is a method that involves carrying out polymerization without using a crosslinking agent in the polymerization temperature range of 106 to 160° C. As is shown in its example, it is disclosed that a dried solid having a low water content is obtained when the polymerization is completed. In a gazette of JP-A-318022/1989 (Mitsubishi Petrochemical Co., Ltd.), disclosed is a method which involves polymerizing an aqueous solution including a monomer having a neutralization ratio of 20 to 50 mol % in an amount of 45 to 80 weight %, and obtaining a polymerized product nearly in a dry state. However, these methods have demerits such that the extractable content of formed water-absorbent resins is relatively large in comparison with their absorption capacity.

In addition, in gazettes of JP-A-147512/1980 (Sumitomo Chemical Co., Ltd.), JP-A-147809/1981 (Sumitomo Chemical Co., Ltd.), JP-A-275607/1988 (Sanyo Chemical Industries, Ltd.), and JP-A-275608/1988 (Sanyo Chemical Industries, Ltd.), it is disclosed that: a dried product of water-absorbent resin is obtained at a stroke by supplying an aqueous monomer solution onto a heated rotation drum, and then scratching and collecting the resultant product. In a gazette of JP-A-165610/1989 (Rohm and Haas Company), it is disclosed that a substantially dried solid water-absorbent resin is also obtained by supplying an aqueous monomer solution onto a heated face in the nearly same way. However, these methods also have demerits such that the extractable content of formed water-absorbent resins is relatively large in comparison with their absorption capacity.

In addition, in a gazette of JP-A-215801/1990 (Mitsubishi Petrochemical Co., Ltd.), it is disclosed that: the heat of neutralization of a monomer is utilized, and then the polymerization is carried out by spraying a heated aqueous monomer solution in a gas phase. However, the control of the polymerization is thought to be difficult because the polymerization is completed within about 3 seconds.

The above prior arts were techniques as disclosed before 1990, but each has demerits. Therefore, it seems that they are not carried out actually.

Thereafter, disclosed are techniques for enhancing performance in order to improve a ratio of performance of the water-absorbent resins to their costs. In gazettes of JP-A-175319/1992 (Sanyo Chemical Industries, Ltd.) and JP-A-181005/1999 (Nippon Shokubai Co., Ltd.), it is disclosed that: an attempt is made to obtain water-absorbent resins having high performance by initiating polymerization at a low temperature, mildly carrying out the polymerization while being cooled, and thereby suppressing the peak temperature to not higher than about 90° C. In a gazette of JP-A-228604/1999 (Nippon Shokubai Co., Ltd.), it is disclosed that: an attempt is made to obtain water-absorbent resins having high performance by also initiating polymerization at a low temperature, mildly carrying out the polymerization while being cooled, and thereby suppressing the peak temperature to not higher than about 95° C. or controlling the amount of the solid component concentration as increased in the range of 0.2 to 10 weight %. In addition, in WO 01/38402A1 (BASF), it is disclosed that: an attempt is made to obtain water-absorbent resins having high performance by also initiating polymerization at a low temperature, and cooling from a polymerization vessel wall and discharging the resultant polymerized gel in order to suppress the consumption of heat of reaction (e.g. in order to suppress the peak temperature to not higher than about 100° C.). In agazette of JP-A-067404/1997 (BASF) and a specification of U.S. Pat. No. 6,187,828 (BASF), disclosed is a method that involves initiating polymerization at a low temperature in a cylindrical polymerization vessel, and then adiabatically carrying out the polymerization. However, the cooling is not carried out, and therefore the method has demerits such that the concentration of the aqueous monomer solution cannot be increased, namely, demerits such that the residence time is prolonged (a few hours). Both of these are carried out at the sacrifice of productivity, and therefore it is inevitable to need great costs.

In addition, recently, in Journal of Applied Polymer Science, Vol. 74, 119 to 124 (1999), report was "An Efficient Preparation Method for Superabsorbent Polymers" (Chen. Zhao). This proposes a low-cost polymerization method which involves charging an aqueous solution having a monomer concentration of 43.6% and an initiator in a stainless-steel-made petri dish, immersing the petri dish in a water bath of 70 or 80° C., and then carrying out polymerization, but the method has not reached an industrially useful level.

In addition, in a gazette of JP-A-045812/1998 (Selisui Plastics Co., Ltd.), it is disclosed that an attempt is made to prevent bumping, to improve emission of vapor, and to lower the water content of formed gel, by adding a short fiber to an aqueous monomer solution. However, it has demerits of using the valuable short fiber that does not contribute to water absorption.

DISCLOSURE OF THE INVENTION
Object of the Invention

An object of the present invention is to provide a process for producing a water-absorbent resin having excellent performance at low cost. More particularly, the object is to provide: a base polymer, which displays high absorption capacity without load and has a small extractable content; and a water-absorbent resin, which is surface-crosslinking-treated and displays high absorption capacity under a load, by reasonable steps.

SUMMARY OF THE INVENTION

The present inventors diligently studied in order to attain the above-mentioned object. As a result, they have found out that: contrary to the prior established theory (that water-absorbent resins having high performance are obtained by initiating polymerization at a low temperature, and cooling in order to lower the peak temperature to the utmost, as disclosed in gazettes of JP-A-175319/1992 (Sanyo Chemical Industries, Ltd.), JP-A-181005/1999 (Nippon Shokubai Co., Ltd.), and JP-A-228604/1999 (Nippon Shokubai Co., Ltd.)), water-absorbent resins having high performance are obtained with high productivity by an innovative method in view of the prior theory, which method involves obtaining a hydrogel having a high solid component concentration in a short time surprisingly by raising the temperature of an aqueous monomer solution as supplied into a polymerization vessel having shear force (causing shearing action), and evaporating water at a boiling temperature of water in the gel. Then, the present invention has been completed. Herein, the term "hydrogel" means a water-absorbent resin having a solid component concentration of not more than 82 weight (mass) %.

In addition, in the production process for a water-absorbent resin, it is important how a hydrogel being formable in the polymerization and having a high solid component concentration of 55 to 82 weight % can be disintegrated. When a hydrogel, as formed by carrying out aqueous solution polymerization of a monomer component that is converted to water-absorbent resins by the polymerization, has such a shape (e.g. thick plate, block, and sheet) as is difficult to dry as it is, the hydrogel is usually disintegrated, and thereafter water-absorbent resin products are produced through each step of such as drying, pulverization, classification, and surface treatment. In the case of a water-absorbent resin of an acrylic acid (salt) type, a hydrogel can easily be disintegrated with such as a meat-chopper-type disintegrator when the hydrogel has a solid component concentration of less than 55 weight %. In addition, when the solid component concentration is more than 82 weight %, the hydrogel can easily be pulverized with such as a conventional shock-type pulverizer in the same way as of a dried polymer. However, the hydrogel having a solid component concentration of 55 to 82 weight % is difficult to handle because of its properties, and therefore an attempt to industrially disintegrate the hydrogel has not been successful yet.

In such as Comparative Examples 1 and 2 of a specification of U.S. Pat. No. 4,703,067 (American Colloid), hydrogels having solid component concentrations of 58% and 67% respectively were obtained, but it is described therein as follows: "They could not be pulverized as they were, and it was necessary to dry them before the pulverization.", and the disintegration in the above solid component concentration range is avoided.

Examples of disintegrators for gels are described in a gazette of JP-A-175319/1992 (Sanyo Chemical Industries, Ltd.). The polymerization is carried out in a monomer concentration of 50 weight % at the maximum, but shown is no disintegration example of a hydrogel having a solid component concentration of not less than 55 weight %.

In gazettes of JP-A-119042/1998 (Nippon Shokubai Co., Ltd.), JP-A-188725/1999 (Nippon Shokubai Co., Ltd.), JP-A-188726/1999 (Nippon Shokubai Co., Ltd.), it is disclosed that gels are disintegrated by shearing with fixed and rotary cutters, but shown is no disintegration example of a hydrogel having a solid component concentration of not less than 55 weight %, either.

In a gazette of JP-A-188727/1999 (Nippon Shokubai Co., Ltd., invented by Mr. Hatsuda, Mr. Miyake, and Mr. Yano), it is disclosed that: a hydrogel is sheared by holding it between a pair of spiral rotary cutters which are settled facing each other and have different advancing speeds, and then disintegrated. In its Example 1, a hydrogel having a water content of 39 weight % is disintegrated, but there is no disintegration example of a hydrogel having a weight-average particle diameter of not larger than 100 mm. Actually, the weight-average particle diameter of the hydrogel as disintegrated is larger than 100 mm.

Accordingly, the present inventors diligently studied the above matters. As a result, they have established a production process for a water-absorbent resin by applying an aqueous monomer solution having a temperature of not lower than a specific temperature to a specific polymerization method, which process does not need the disintegration methods for a hydrogel as mentioned above.

That is to say, a production process for a water-absorbent resin, according to the present invention, comprises a polymerization step that includes the steps of: supplying an aqueous solution of a water-soluble unsaturated monomer component including a major proportion of acrylic acid and/or its salt into a polymerization vessel causing shearing action; and then carrying out polymerization, involving crosslinking, of the water-soluble unsaturated monomer and at the same time carrying out fine division of the resultant hydrogel; with the production process being characterized in that the aqueous solution of the water-soluble unsaturated monomer component as supplied into the polymerization vessel has a temperature of not lower than 40° C.

In addition, a water-absorbent resin, according to the present invention, is a water-absorbent resin which is obtained by the present invention production process, and which displays an absorption capacity of not less than 20 g/g under a load.

In addition, a sanitary article, according to the present invention, comprises the present invention water-absorbent resin.

DETAILED DESCRIPTION OF THE INVENTION

Hereinafter, the modes for carrying out the present invention are explained in detail.

Examples of the water-soluble unsaturated monomer component as used in the present invention include: anionic unsaturated monomers, such as (meth)acrylic acid, maleic acid or maleic anhydride, itaconic acid, cinnamic acid, vinylsulfonic acid, allyltoluenesulfonic acid, vinyltoluenesulfonic acid, styrenesulfonic acid, 2-(meth)acrylamido-2-methylpropanesulfonic acid, 2-(meth)acryloylethanesulfonic acid, 2-(meth)acryloylpropanesulfonic acid, 2-hydroxyethyl (meth)acryloyl phosphate, and salts thereof; mercaptane-group-containing unsaturated monomers; phenolic-hydroxyl-group-containing unsaturated monomers; amide-group-containing unsaturated monomers, such as (meth)acrylamide, N-ethyl(meth)acrylamide, and N,N-dimethyl(meth)acrylamide; amino-group-containing unsaturated monomers, such as N,N diethylaminoethyl (meth)acrylate, N,N dimethylaminopropyl (meth)acrylate, and N,N-dimethylaminopropyl (meth)acrylamide.

These monomers may be used either alone respectively or fitly in combinations with each other. However, in view of performance and costs of the water-absorbent resin as obtained, it is necessary to use acrylic acid and/or its salts (e.g. salts of such as sodium, lithium, potassium, ammonium, and amines; of the above, its sodium salt is favorable in view of costs) as main components. The ratio of the acrylic acid and/or its salts is favorably not less than 70 mol %, more favorably not less than 80 mol %, still more favorably not less than 90 mol %, particularly favorably not less than 95 mol %, relative to the entire monomer component The solid component concentration in the aqueous solution of the water-soluble unsaturated monomer component as mentioned herein may contain the unsaturated monomer component such as the acrylic acid and/or its salts, and the internal-crosslinking agent, and besides, other additives such as polymerization initiators as mentioned below.

Publicly hitherto known internal-crosslinking agents can be used as the above internal-crosslinking agent. Specific examples include internal-crosslinking agents as described in page 4 of a gazette of JP-A-182750/1998. In consideration of reactivity, one kind or at least two kinds of these can be used. Of the above, it is favorable to essentially use a compound having at least two polymerizable unsaturated groups. The amount of these as used can fitly be determined depending upon desired properties of the water-absorbent resin.

There is no especial limitation on the concentration of the water-soluble unsaturated monomer component in the aforementioned aqueous solution, but the concentration is favorably not less than 30 weight %, more favorably not less than 35 weight %, still more favorably not less than 40 weight %, still more favorably not less than 45 weight %, still more favorably not less than 50 weight %, still more favorably not less than 55 weight %, still more favorably in the range of 30 to 70 weight %, still more favorably 35 to 60 weight %, still more favorably 40 to 60 weight %. In the case where the concentration is less than 30 weight %, the productivity is low. In the case where the concentration is more than 70 weight %, the absorption capacity is lowered.

When an acid-group-containing monomer is used, there is no especial limitation on its neutralization ratio. However, it is also considered that the neutralization after the polymerization is favorably unnecessary in uses possibly contacting with human bodies, such as sanitary articles, and therefore the neutralization ratio is favorably not less than 50 mol %, more favorably in the range of 50 to 80 mol % (excluding 80 mol %), still more favorably 55 to 78 mol %, most favorably 60 to 75 mol %.

When the acrylic acid is neutralized with an alkali and then used, it is favorable to effectively utilize heat of neutralization and/or heat of dissolution (of the acrylic acid and the alkali) for heating to raise the temperature of the aqueous solution of the water-soluble unsaturated monomer component. In a favorable mode for carrying out the invention, the polymerization is initiated by adding a crosslinking agent and an initiator to an aqueous solution of the water-soluble unsaturated monomer component, of which the temperature is raised by the neutralization in an adiabatic state, or as is mentioned below, the heat of neutralization and/or the heat of dissolution (of the acrylic acid and the alkali) is utilized to remove dissolved oxygen.

When the polymerization is carried out, hydrophilic polymers (e.g. starch, derivatives of starch, cellulose, derivatives of cellulose, polyvinyl alcohol, poly(acrylic acid (salts)), and crosslinked products of poly(acrylic acid (salts))), chain transfer agents (e.g. hypophosphorous acid (salts)), and chelating agents may also be added to the reaction system.

As to the polymerization method for the above monomer component, used is a polymerization step that includes the steps of: supplying an aqueous solution of a water-soluble unsaturated monomer component including a major proportion of acrylic acid and/or its salt into a polymerization vessel causing shearing action (having shear force); and then carrying out polymerization, involving crosslinking, of the water-soluble unsaturated monomer and at the same time carrying out fine division of the resultant hydrogel. Such the polymerization method is carried out, and therefore the hydrogel as discharged from the polymerization vessel can be introduced into a drying step as it is, and surplus facilities (for the fine division of the gel) such as hydrogel disintegrators are especially unnecessary, and the polymerization can be carried out very reasonably and at low cost As to the polymerization vessel causing shearing action (having shear force) as used herein, even single-shaft agitation machines can be used, but agitation machines having at least two agitation shafts (e.g. twin-arm kneaders) are favorably used. More favorably used are polymerization vessels having a rotation agitation shaft, in which the continuous polymerization that involves continuously supplying the aqueous solution of the water-soluble unsaturated monomer component and continuously discharging the resultant hydrogel can be carried out. Particularly favorably used are polymerization vessels having at least two rotation agitation shafts. Examples thereof include triple-shaft kneaders (kneader-ruders) having two agitation paddles and one discharging screw, and twin-shaft-extruding kneaders or blenders. Of the above, the most favorable polymerization vessels for obtaining water-absorbent resins having high performance with high productivity are continuous kneaders having piston flowability, which have two rotation agitation shafts in such a manner that the aqueous solution of the water-soluble unsaturated monomer component is continuously supplied into the polymerization vessel and the resultant hydrogel is continuously discharged. In the case of using the aforementioned continuous kneaders, the productivity is greatly improved in comparison with batchwise polymerization vessels. When the polymerization is carried out by supplying the aqueous solution of the water-soluble unsaturated monomer component into such as a batchwise polymerization vessel, the polymerization reaction in the present invention proceeds violently while being vapored and swollen. Therefore, from the viewpoint of safety, the amount of the aqueous solution of the monomer component as supplied cannot help being reduced. In addition, time is also necessary to discharge the hydrogel. On the other hand, in the case of using the continuous kneaders as the polymerization vessels, the aqueous solution of the monomer component can be supplied continuously, and the resultant hydrogel is continuously discharged. Therefore, the high productivity is obtained.

Furthermore, in order to prevent such as adhesion of useless gels, the surface roughness of the inner faces of these polymerization vessels is favorably reduced by resin-coating with such as Teflon (registered trade mark) or by electrolysis grinding, and polymerization vessels having stainless-steel-made inner faces are particularly favorably used. Furthermore, the polymerization vessel is favorably cooled or heated with a jacket from the outside, and further the agitation paddles themselves are also favorably equipped with a cooling or heating structure by installing medium passageways therein. In addition, the volume of the polymerization vessel is fitly determined, and is usually favorably in the range of 0.001 to 10 m$^3$, and the aqueous solution of the monomer component is favorably charged in an amount of 10 to 90%, more favorably 20 to 70%, relative to the volume.

In addition, the rotation agitation shafts existing in these polymerization vessels are rotated for at least a predetermined time during the polymerization, and then the fine division of the hydrogel is carried out. The rotation speed may be constant or changeable, or the rotation may be stopped temporarily or intermittently. Specifically, the static polymerization and the rotation polymerization (shear polymerization) may be carried out together in the polymerization vessel causing shearing action (having shear force). Furthermore, when at least two agitation shafts are used, these agitation shafts may be rotated in the same direction or in different directions, but at least two agitation shafts are favorably in the different directions toward the inside. In addition, the rotation speeds of both may be identical or different.

Specific examples of the polymerization vessels causing shearing action (having shear force) are as follows:

Twin-arm kneader (KNEADER, Kurimoto, Ltd.);
Twin-arm kneader-ruder (KNEADER-RUDER, Moriyama Co., Ltd.);
Continuous kneader (CONTINUOUS KNEADER, Dalton Co., Ltd.);
Paddle dryer (PADDLE DRYER, Nara Kikai Seisakusho Co., Ltd.);
KRC kneader (KURIMOTO-READCO CONTINUOUS KNEADER, Kurimoto, Ltd.);
Extruder (EXTRUDER, Kurimoto, Ltd.);
Honda De-Airing Extruder (HONDA DE-AIRING EXTRUDER, Honda Tekko Co., Ltd.);
Chopper (CHOPPER, Hiraga Kosakusho Co., Ltd.);
Twin-Dome Gran (TWIN-DOME GRAN, Fuji Powdal Co., Ltd.); and
Bivolak (BIVOLAK, Sumitomo Heavy Industries. Ltd.).

In radical aqueous solution polymerization, the dissolved oxygen that inhibits the polymerization is generally removed by blowing inert gas or by carrying out deaeration under a reduced pressure before the addition of the polymerization initiator. However, it costs expenses for facilities and operation therefor in actual circumstances. In the favorable mode for carrying out the present invention, the operation of removing the dissolved oxygen is carried out by utilizing the heat of neutralization and/or the heat of dissolution (hydration) (of the acrylic acid and the alkali) as mentioned above, and heating to raise the temperature of the aqueous solution of the monomer component, and thereby vaporizing the dissolved oxygen out.

In more favorable mode for carrying out the invention, the temperatures of such as acrylic acid, an aqueous alkali solution, and water as raw materials for the aqueous solution of the monomer component are raised by the neutralization without beforehand deoxidization, and the amount of the dissolved oxygen is favorably adjusted to not larger than 4 ppm, more favorably not larger than 2 ppm, most favorably not larger than 1 ppm, relative to the aqueous solution of the monomer component, and then they are subjected to the polymerization without the deoxidization operation as they are.

In addition, it is also favorable that: some or all of such as the acrylic acid, aqueous alkali solution, and water as raw materials for the aqueous solution of the monomer component are beforehand partially deoxidized, and they are further deoxidized by the rise of the temperature due to the neutralization. In addition, when the polymerization is initiated at a high temperature of not lower than 80° C. by carrying out line-mixing neutralization of the acrylic acid and the alkali and further line-mixing a polymerization initiator, it is favorable that the deoxidization of such as the raw acrylic acid, aqueous alkali solution, and water is not carried out beforehand in order to prevent the polymerization from initiating in the line.

The polymerization is usually carried out under an atmospheric pressure, but it is also a favorable mode that the polymerization is carried out under a reduced pressure with distilling off water in order to lower the boiling temperature of the polymerization system. The polymerization is more favorably carried out under an atmospheric pressure because of such as easiness of operation.

There is no especial limitation on the increase of the neutralization ratio during the polymerization, but the increase of the neutralization ratio is favorably not less than 2 mol %, more favorably not less than 3 mol %, still more favorably not less than 4 mol %. Even if the increase of the neutralization ratio is zero, there is no especial problem. However, in the case where the increase of the neutralization ratio is not less than 2 mol %, there are advantages in that the properties of the polymer as obtained (e.g. hydrogel, base polymer, or water-absorbent resin) are improved.

There is no especial limitation on the polymerization initiator usable in the present invention. Usable are such as pyrolysis-type initiators (e.g. persulfate salts, such as sodium persulfate, potassium persulfate, and ammonium persulfate; peroxides, such as hydrogen peroxide, t-butyl hydroperoxide, and methyl ethyl ketone peroxide; and azo compounds, such as azonitrile compounds, azoamidine compounds, cyclic azoamidine compounds, azoamide compounds, alkylazo compounds, 2,2'-azobis(2-amidinopropane) dihydrochloride, and 2,2'-azobis[2-(2-imidazolin-2-yl)propane]dihydrochloride)) and photolysis-type initiators (e.g. benzoin derivatives, benzyl derivatives, acetophenone derivatives, benzophenone derivatives, and azo compounds). The persulfate salts are favorable in view of ability to lower costs and residual monomers. In addition, the use of the photolysis-type initiator and ultraviolet ray is also a favorable method, and it is more favorable to use the photolysis-type initiator and the pyrolysis-type initiator together.

It is favorable to beforehand raise the temperature of the aqueous solution of the monomer component as supplied into the polymerization vessel. The reason is because the aforementioned dissolved oxygen is easily removed by doing such, and also because the favorable polymerization initiation temperature as mentioned below can be realized at once. There is no especial limitation on such the temperature of the aqueous solution of the monomer component, but the temperature is usually not lower than 40° C., favorably not lower than 50° C., more favorably not lower than 60° C., more favorably not lower than 70° C., more favorably not lower than 80° C., more favorably not lower than 90° C., more favorably in the range of 80 to 105° C., most favorably 90 to 100° C. In the case where the temperature is lower than 40° C., not only the productivity is lowered because of prolonging the induction period and polymerization time, but also the properties of the water-absorbent resin are deteriorated. Incidentally, the induction period means how long time passes since the aqueous solution of the monomer component and the aqueous initiator solution are blended until the polymerization is initiated, and the polymerization time means how long time passes since the aqueous solution of the monomer component is supplied into the polymerization vessel until the resultant hydrogel is discharged from the polymerization vessel.

Incidentally, in order to ensure the temperature of this aqueous solution of the monomer component and to cause the polymerization initiation, as is mentioned above, the heat of neutralization and/or the heat of dissolution (of the acrylic acid and the alkali) of the aqueous solution of the monomer component are favorably utilized.

In addition, it is favorable to introduce the initiator into the aqueous solution of the monomer component as supplied into the polymerization vessel. The reason is because: when the temperature of the aqueous solution of the monomer component is, for example, adjusted to not lower than 40° C. in the polymerization vessel, the polymerization is initiated as soon as the initiator is added thereto, and the mode of the polymerization seems to be the same mode as of the present invention in appearance, but the polymerization proceeds so fast that the blending of the polymerization initiator is insufficient (non-uniform), and the high extractable content is caused. Furthermore, there is also a problem such that the polymerization is initiated while the aqueous solution of the monomer component is heated (before the addition of the initiator). In this connection, when the temperature of the aqueous solution of the monomer component is lower than 40° C., the mode of the polymerization is not different from conventional modes in any way, and the polymerization does not attain such high productivity and high performance as obtained in the present invention.

There is no especial limitation on the highest temperature of the hydrogel in the polymerization vessel. Its minimum value is favorably not lower than 100° C., and its maximum value is favorably not higher than 150° C., more favorably not higher than 140° C., more favorably not higher than 130° C., more favorably not higher than 120° C., more favorably not higher than 115° C. The highest temperature is most favorably in the range of 100 to 115° C. In the case where the highest temperature is higher than 150° C., there are disadvantages in that the properties of the polymer as obtained (e.g. hydrogel, base polymer, or water-absorbent resin) are extremely deteriorated.

In the present invention, the difference $\Delta T$ between the temperature of the aqueous solution of the monomer component as supplied into the polymerization vessel and the highest temperature of the hydrogel in the polymerization vessel is favorably not higher than 70° C., more favorably not higher than 60° C., still more favorably not higher than 50° C., still more favorably not higher than 40° C., still more favorably not higher than 30° C., most favorably not higher than 25° C. In the case where the $\Delta T$ is higher than 70° C., there are disadvantages in that the properties of the polymer as obtained (e.g. hydrogel, base polymer, or water-absorbent resin) are deteriorated.

There is no especial limitation on the polymerization time, but it is favorably not more than 10 minutes, more favorably not more than 5 minutes, more favorably less than 5 minutes, more favorably not more than 3 minutes. In the case where the polymerization time is more than 10 minutes, there are disadvantages in that the productivity of the polymer as obtained (e.g. hydrogel, base polymer, or water-absorbent resin) is lowered.

Thus, in the present invention, the induction period and the polymerization time are shortened very much, and therefore it is also easy to add a fine powder of at least one member selected from the group consisting of a hydrogel, a base polymer and a surface-crosslinked water-absorbent resin as formed together with the production, either to the aqueous solution of the monomer component or at the same time as the supply of the aqueous solution of the monomer component. Incidentally, herein, a water-absorbent resin fine powder contains powders passing through a sieve having a mesh opening size of 150 μm in not less than 70 weight %. In this connection, when the fine powder is added to the aqueous solution of the monomer component in the hitherto polymerization as initiated at a low temperature, the polymerization time is long. Therefore, there are problems such that: the monomer is absorbed in the fine powder, and the residual monomer is increased, and the absorption capacity is difficult to adjust. Even if they are added thereto, a method such that the amount as added is decreased in order to preserve the properties has been carried out.

According to favorable examples of the polymerization method in the present invention, the polymerization goes on, while the temperature of the system rapidly rises after the initiation of the polymerization and reaches a boiling point with a low polymerization conversion of such as 10 to 20 mol %, and water vapor is generated, and the solid component concentration is increased. The heat of the polymerization is effectively utilized, and the solid component concentration is increased. Therefore, it is desirable to suppress heat radiation from connecting material portions of the polymerization vessel to the utmost. Favorable used are such as polymerization vessels in which the non-connecting material portions. (comprised of resins, rubbers, or stainless steel as the material quality) are covered with heat-retaining materials, or polymerization vessels as heated with jackets. The water vapor as generated from the system may contain the monomer, and therefore it is desirable to recover and reuse (recycle) it in such a case. Particularly, it is favorable that the acrylic acid and/or water having vaporized during the polymerization are collected and then reused (recycled). The recovery ratio of the acrylic acid is favorably not less than 1%, more favorably not less than 2%, still more favorably not less than 3%, of the weight of the entire acrylic acid (before the neutralization) as used.

Incidentally, as to the recovery method for the water vapor as generated from the system, effective is a method that involves recovering the water vapor while introducing a gas into the polymerization vessel or aspirating the water vapor therefrom. In addition, in the case of introducing the above gas, there are many cases where inert gas containing no oxygen is generally used in order to decrease the residual monomer in the hydrogel. However, the present invention is characterized by enabling the polymerization time to shorten, and by enabling to obtain a water-absorbent resin, in which the amount of the residual monomer is little because the water vapor has been generated severely from the hydrogel during the polymerization even if oxygen-containing gas may be used.

In addition, the present invention process is characterized in that the polymerization is carried out at a high temperature from the initiation of the polymerization, and the above characteristic seems to cause high performance. In the polymerization under an atmospheric pressure, a favorable mode is the polymerization such that: the temperature has already been not lower than 100° C. when the polymerization conversion is 40 mol %, and the temperature has also been not lower than 100° C. when the polymerization conversion is 50 mol %. A more favorable mode is the polymerization such that: the temperature has already been not lower than 100° C. when the polymerization conversion is 30 mol %, and the temperature has also been not lower than 100° C. when the polymerization conversion is 50 mol %. The most favorable mode is the polymerization such that: the temperature has already been not lower than 100° C. when the polymerization conversion is 20 mol %, and the temperature has also been not lower than 100° C. when the polymerization conversion is 50 mol %. In the polymerization under a reduced pressure, a favorable mode is the polymerization such that: the temperature has already reached a boiling temperature when the polymerization conversion is 40 mol %, and the temperature has also been the boiling temperature when the polymerization conversion is 50 mol %. A more favorable mode is the polymerization such that: the temperature has already reached a boiling temperature when the polymerization conversion is 30 mol %, and the temperature has also been the boiling temperature when the polymerization conversion is 50 mol %. The most favorable mode is the polymerization such that: the temperature has already reached a boiling temperature when the polymerization conversion is 20 mol %, and the temperature has also been the boiling temperature when the polymerization conversion is 50 mol %.

In this way, the temperature is high with a low polymerization conversion, and therefore the polymerization time as required is also short, and the polymerization is usually finished within 10 minutes, more favorably within 5 minutes. Herein, the polymerization time as required means how long time passes since the aqueous solution of the monomer component as obtained by adding the polymerization initiator is supplied into the polymerization vessel until the resultant hydrogel is discharged from the polymerization vessel.

In addition, as to the timing of the addition of the initiator, the aqueous solution of the monomer component and the aqueous initiator solution may be blended in the polymerization vessel, but it is favorable that the aqueous solution of the monomer component and the aqueous initiator solution are blended before they are supplied into the polymerization vessel. There is a more favorable method in which the aqueous solution of the monomer component and the aqueous initiator solution are blended just before they are supplied into the polymerization vessel.

In addition, in order to prevent the initiation of the polymerization and the clogging of such as supplying lines before supplying a mixed solution of the aqueous solution of the monomer component and the aqueous initiator solution into the polymerization vessel, such as polymerization inhibitors can also be made to exist in the monomer. There is no especial limitation on the polymerization inhibitor, and effective are such as: o-, m-, or p-methoxyphenol, and methoxyphenols further having one or at least two substitutent groups (e.g. a methyl group, a t-butyl group, and a hydroxyl group) (particularly favorably p-methoxyphenol); and other hydroquinones, copper salts, and methylene blue. They may be used either alone respectively or in combinations with each other. It is favorable that the polymerization inhibitor is usually made to exist in acrylic acid as used for preparing the aqueous solution of the monomer component. Specifically, in the present invention, one of the favorable modes is to use acrylic acid containing p-methoxyphenol as the water-soluble unsaturated monomer component. The amount of the polymerization inhibitor existing in the above acrylic acid is favorably not larger than 200 weight ppm, more favorably in the range of 10 to 160 weight ppm. In addition, also exemplified is a method that involves delaying the polymerization initiation time without entirely removing such as furfural in a purification step for producing the above acrylic acid.

In the present invention, it is desirable to carry out the polymerization while water is vaporized in such a manner that: the concentration ratio, which is defined as a ratio of a solid component concentration of the hydrogel as discharged from the polymerization vessel to a solid component concentration of the aqueous solution of the monomer component as supplied into the polymerization vessel, is favorably not less than 1.10, more favorably not less than 1.15, still more favorably not less than 1.20, particularly favorably not less than 1.25. In the case where the concentration ratio is less than 1.10, it cannot be said that the utilization of the heat of the polymerization is sufficient. Herein, the solid component of the aqueous solution of the monomer component means the monomer and other additives, and does not include water and solvents.

As to the solid component concentration of the hydrogel as obtained by the present invention, its maximum value is favorably not more than 82 weight %, more favorably not more than 75 weight %, and its minimum value is favorably not less than 50 weight %, more favorably not less than 55 weight %. In addition, the solid component concentration is favorably in the range of 50 to 80 weight %, more favorably 55 to 75 weight %. In the case where this solid component concentration is more than 82 weight %, observed is the deterioration of performance, namely, the lowering of absorption capacity and the increase of extractable content In addition, in the case where the solid component concentration is less than 50 weight %, there are disadvantages in that the drying in a following step bears a heavy burden.

The above hydrogel favorably has a form that is formed by foaming expansion and contraction during the polymerization. This is a form made by a manner that: the polymerization system is foamed to have a foam diameter of several millimeters to several centimeters in unit by the water vapor pressure as caused by the boiling during the polymerization, and then its surface area is increased, and thereby the vaporization of the water vapor is promoted, and thereafter the foam is contracted. In addition, this form also has an unexpected characteristic such that: the peeling ability from the polymerization vessel is improved, or the fine division or disintegration of the hydrogel is made easy.

A base polymer (water-absorbent resin before surface-crosslinking treatment) can be obtained by drying and pulverizing the above hydrogel.

When the base polymer as obtained is observed with a microscope, the bubble size is comparatively large even in the case where the polymerization accompanies the foaming. Therefore, the major proportion of particles is in a noncrystalline form containing no bubble.

In the present invention production process, the surface-crosslinking treatment of the base polymer may further be carried out, and thereby a water-absorbent resin having a large absorption capacity under a load can be obtained. In the surface-crosslinking treatment, usable are publicly known surface-crosslinking agents and publicly known surface-crosslinking methods that are usually used for the above uses.

Incidentally, in the present specification, the terms such as hydrogel, base polymer, and surface-crosslinked water-absorbent resin are used, but any one is a term that represents one form of water-absorbent resins.

The present invention production process has one great characteristic such that the finely divided hydrogel having a high solid component concentration of 55 to 82 weight % as discharged from the polymerization vessel can be introduced into dryers without using such as other disintegrators. However, when the occasion demands, the finely divided hydrogel as obtained by the present invention production process can also be disintegrated to further make the drying efficiency and pulverization step easy. Then, the disintegration method comes into question. In the case of the water-absorbent resin of an acrylic acid (salt) type, the hydrogel can easily be disintegrated with such as a meat-chopper-type disintegrator when the hydrogel has a solid component concentration of less than 55 weight %. In addition, when the solid component concentration is more than 82 weight %, the hydrogel can easily be pulverized with such as a conventional shock-type pulverizer in the same way as of a dried hydrogel. However, the hydrogel having a solid component concentration of 55 to 82 weight % is difficult to handle because of its properties, and therefore an attempt to industrially disintegrate the hydrogel has not been successful yet.

Accordingly, the present inventors diligently studied how the hydrogel having a high solid component concentration of 55 to 82 weight % formable in the polymerization can be disintegrated. As a result, they have found out that the fine division can easily be carried out with specific disintegrators and pulverizers (these are represented by the term "disintegrators" in the present patent application.).

Incidentally, there is no especial limitation on the shape of the hydrogel having a solid component concentration of 55 to 82 weight % as subjected to the disintegration, but the weight-average particle diameter of the hydrogel is favorably not larger than 5 cm, more favorably not larger than 3 cm.

A disintegrator having a screen is favorable as an apparatus for disintegrating the hydrogel having a solid component concentration of 55 to 82 weight % in the present invention. Furthermore, the above disintegrator is favorably an apparatus corresponding to shear-type crushers or cutting-shearing mills as described in "Table 16.4, Classification of pulverizers" of *"Chemical Engineering Handbook* (sixth edition, edited by the Chemical Engineering Society, Maruzen Co., Ltd., 1999)". The disintegrator is more favorably an apparatus in which the disintegration is carried out by shearing with fixed and rotary cutters. The disintegration of the hydrogel having a high solid component concentration of 55 to 82 weight % can easily be carried out by the disintegration with these apparatuses; which has hitherto been difficult.

Specific examples of the shear-type crushers and cutting-shearing mills are as follows:

Saw, Round saw, and Band saw (BAND SAW);
Vertical pulverizer (VERTICAL CUTTING MILL, Orient Co., Ltd.);
Rotoplex (ROTOPLEX, Hosokawa Micron Co., Ltd.);
Turbo cutter (TURBO CUTTER, Turbo Industry Co., Ltd.);
Turbo grinder (TURBO GRINDER, Turbo Industry Co., Ltd.);
Tyre shredder (TYRE SHREDDER, Masuno Seisakusho Co., Ltd.);
Rotary cutter mill (ROTARY CUTTER MILL, Yoshida Seisakusho Co., Ltd.);
Cutter mill (CUTTER MILL, Tokyo Atomizer Production Co., Ltd.);
Shred crusher (SHRED CRUSHER, Tokyo Atomizer Production Co., Ltd.);
Cutter mill (CUTTER MILL, Masuko Sangyo Co., Ltd.);
Crusher (CRUSHER, Masuko Sangyo Co., Ltd.);
Rotary cutter mill (ROTARY CUTTER MILL, Nara Kikai Seisakusho Co., Ltd.);
Gainax crusher (GAINAX CRUSHER, Horai Co., Ltd.);
U-com (U-COM, Horai Co., Ltd.); and
Meshmill (MESHMILL, Horai Co., Ltd.).

In the present invention, it has been found out that: when the hydrogel having a solid component concentration of 55 to 82 weight % is disintegrated with a disintegrator, such the hydrogel difficult to disintegrate is disintegrated even with disintegrators except for cutting-type ones, by either one or both of favorably increasing the solid component concentration by not less than 2 weight % (e.g. if the solid component concentration is 72 weight % after disintegrating a hydrogel having a solid component concentration of 70 weight %, the solid component concentration is increased by 2 weight %.) and blowing gas (favorably dry air) into the disintegrator.

As to the increase of the solid component concentration, as the increasing ratio rises higher than 2 weight % (e.g. 3 weight % or 4 weight %), or as the quantity of the wind as blown is larger, the disintegration is more easily carried out. However, they should be selected in consideration of economy. The water vapor as generated from the hydrogel is condensed in the apparatus during the disintegration, and thereby easily causes adhesion and clogging of the hydrogel in the apparatus. However, it is thought difficult to cause such a phenomenon by the ventilation.

In addition, when the disintegration is carried out, surfactants as mentioned in a gazette of JP-A-188726/1999 (Nippon Shokubai Co., Ltd.) may be added thereto. However, the higher the solid component concentration of the hydrogel is, the lower its necessity is.

The weight-average particle diameter of the hydrogel as disintegrated by the present invention disintegration means is favorably not larger than 100 mm, more favorably not larger than 10 mm, still more favorably not larger than 3 mm, most favorably not larger than 1 mm. It is ideal that the disintegration can be carried out in the form of hydrogel until obtaining particles having particle diameters of final products.

There is no especial limitation on the amount of the residual monomer of: the finely divided hydrogel as discharged from the polymerization vessel in the present invention; and the hydrogel as obtained by disintegrating the above hydrogel by the present invention disintegration means, but the amount of the residual monomer is favorably not larger than 3,000 weight ppm for inhibiting scatter of the residual monomer in such as drying of a following step. Depending upon its use, the amount of the residual monomer is favorably not larger than 1,000 weight ppm, more favorably not larger than 500 weight ppm, most favorably not larger than 300 weight ppm. In the case where the hydrogel itself is particularly used for uses of sanitary articles such as disposable diapers, the amount of the residual monomer is favorably not larger than 1,000 weight ppm, more favorably not larger than 500 weight ppm.

The finely divided hydrogel as discharged from the polymerization vessel in the present invention, and the hydrogel as obtained by disintegrating the above hydrogel by the present invention disintegration means favorably have a solid component concentration of 55 to 82 weight %, an amount of the residual monomer of not larger than 1,000 weight ppm, and a weight-average particle diameter of not larger than 3 mm.

Incidentally, the present invention disintegrated hydrogel having a solid component concentration of 55 to 82 weight %, an amount of the residual monomer of not larger than 1,000 weight ppm, and a weight-average particle diameter of not larger than 3 mm does not include products as obtained by adding water to a hydrogel that is once produced in a dried state (having a solid component concentration of not less than 83 weight %).

In the present invention production process, the hydrogel after the disintegration may be dried. There is no especial limitation on the drying method. The drying may be carried out in such a manner that materials are not moved like a belt-type drying method, but favorable used is a drying method which involves moving materials and further contacting them with such as hot wind and heated faces sufficiently, like such as an agitation drying method, a fluidized-bed drying method, and a gas-flowing drying method.

In the present invention production process, the handling of the hydrogel after being disintegrated can be selected from the following methods:

(1) The hydrogel, as it is, is obtained as a product.; The hydrogel, as it is, is subjected to uses such as sanitary articles and agricultural and horticultural articles. Fine particulate inorganic substances (e.g. bentonite, zeolite, and silicon oxide) may be added thereto for the fluidity of particles.
(2) The surface-crosslinking agent mixes and reacts with the hydrogel, and the resultant mixture in a state of containing water is obtained as a product.; The energy for evaporating water is unnecessary, Fine particulate inorganic substances (e.g. bentonite, zeolite, and silicon oxide) may be added thereto for the fluidity of particles.
(3) The surface-crosslinking agent mixes and reacts with the hydrogel, and the resultant mixture is dried, thus obtaining a product.; The heat energy for the drying can combine the energy for the surface-crosslinking reaction.
(4) The hydrogel is dried, and the resultant dried product, as it is, is obtained as a product.
(5) The hydrogel is dried, and then the resultant dried product is pulverized and classified, thus obtaining a product.
(6) The hydrogel is dried, and then the resultant dried product is pulverized, classified and surface-crosslinked, thus obtaining a product.

The hydrogel having a solid component concentration of 55 to 82 weight %, which has hitherto been difficult to disintegrate, is obtained as a finely divided hydrogel. Therefore, it newly has enabled the following:

1) The above methods (1), (2), and (3) can be carried out
2) Adoptable is a drying method that involves moving materials and further contacting them with such as hot wind and heated faces sufficiently, like such as an agitation drying method, a fluidized-bed drying method, and a gas-flowing drying method having good heat efficiency, which methods have been difficult to use as drying methods unless materials having mold-releaseability (e.g. surfactants) are not added thereto in the drying of the hydrogel having a solid component concentration of less than 55 weight %.
3) The disintegration of the polymer can be carried out in a state of containing water, and therefore a fine powder is difficult to cause, and a particulate hydrogel having little fine powder is obtained.

The water-absorbent resin as surface-crosslinked in the present invention favorably displays an absorption capacity of not less than 20 (g/g) under a load (AAP), more favorably not less than 30 (g/g), still more favorably not less than 35 g/g). In the case where the absorption capacity is less than 20 (g/g), there are disadvantages in that the favorable performance is not displayed when the water-absorbent resin as obtained is used as a sanitary article.

Various functions can also be given by adding, to the present invention water-absorbent resin, such as disinfectants, antimicrobial agents, perfumes, various inorganic powders, foaming agents, pigments, dyes, hydrophilic short fibers, manure, oxidants, reductants, water, and salts, in an amount of favorably not larger than 20 parts by weight, more favorably not larger than 10 parts by weight, in the production process or after the production. Favorable examples of the compounds as added include water-insoluble inorganic powders, and/or polyamines.

The present invention process enables easy production of the water-absorbent resin, which has good absorption properties that are excellent in balance of the absorption capacity without load, absorption capacity under a load, and extractable content. The water-absorbent resin is widely used for water-retaining agents in agricultural and horticultural fields, water-holding materials in engineering works fields, hygroscopic agents, moisture-removing agents, and building materials, but the present invention water-absorbent resin is particularly favorably used for sanitary materials such as disposable diapers, incontinent pads, mother's breast pads, and sanitary napkins.

DETAILED DESCRIPTION OF THE PREFERRED EMBODIMENTS

Hereinafter, the present invention is more specifically illustrated by the following examples and comparative examples. However, the present invention is not limited to these examples. Incidentally, in the examples, unless otherwise noted, the unit "part(s)" denotes "part(s) by weight".

[Measurement of Absorption Capacity Without Load (GV)]

To a nonwoven-fabric-made bag (60 mm×60 mm), 0.2 g of water-absorbent resin was uniformly added, and then immersed in a 0.9 weight % aqueous sodium chloride solution (physiological saline). The bag was pulled up after 30 minutes, and the weight W1 (g) of the bag was measured after draining off at 250×9.81 m/sec$^2$ (250 G) for 3 minutes with a centrifugal separator. The same procedure was carried out without using the water-absorbent resin, and then the weight W0 (g) of the bag was measured. Then, the GV (absorption capacity without load) was calculated from these weights W1 and W0 in accordance with the following equation:

$$GV(g/g) = \{(\text{weight } W1 \text{ (g)} - \text{weight } W0(g))/\text{weight of water-absorbent resin (g)}\} - 1$$

[Extractable Content]

Into a plastic receptacle of 250 ml in capacity having a lid, 184.3 g of 0.9 weight % aqueous NaCl solution (physiological saline) was weighed out. Then, 1.00 g of water-absorbent resin was added to the aqueous solution, and they were stirred for 16 hours, thereby the extractable content in the resin was extracted. This extract liquid was filtrated with a filter paper, and then 50.0 g of the resultant filtrate was weighed out and regarded as a measuring solution.

To begin with, only the physiological saline was firstly titrated with an aqueous 0.1N NaOH solution until the pH reached 10, and then the resultant solution was titrated with an aqueous 0.1N HCl solution until the pH reached 2.7, thus obtaining blank titration amounts ([bNaOH] ml and [bHCl] ml).

The same titration procedure was carried out for the measuring solution, thus obtaining titration amounts ([NaOH] ml and [HCl] ml).

For example, if the water-absorbent resin comprises acrylic acid and its sodium salt, the extractable content and neutralization ratio of the water-absorbent resin can be calculated from their weight-average molecular weights and the titration amounts as obtained from the above procedure, in accordance with the following equation.

neutralization ratio (mol %)={1−([NaOH]−[$b$NaOH])/([HCl]−[$b$HCl])}×100 extractable content (weight %)=0.1×$Mw$×184.3×100×([HCl]−[$b$HCl])/1,000/1.0/150.0

(where: $Mw$=72.06×(1−neutralization ratio/100)+94.04×neutralization ratio/100)

[Measurement of Residual Monomer]

To 1,000 g of deionized water, 0.5 g of water-absorbent resin was added, and extracted for 2 hours under agitation. Thereafter, the resultant swollen-gelled water-absorbent resin was filtrated with a filter paper, and the amount of the residual monomer in the resultant filtrate was analyzed with liquid chromatography. On the one hand, the calibration curve as obtained by analyzing a standard monomer solution having a known concentration in the same way was used as an external standard, and the amount of the residual monomer in the water-absorbent resin was determined in consideration of the dilution ratio of the filtrate.

In addition, the measurement of the residual monomer in the hydrogel was carried out in the same way as of the water-absorbent resin except that: the hydrogel was used in an amount of 0.5 g in terms of solid content, and the immersing time was 24 hours in the deionized water, and the solid content correction was carried out when the residual monomer was calculated.

[Measurement of Solid Content Concentration of Hydrogel]

A small amount of a portion of hydrogel as taken out from a polymerization vessel was cut away and quickly cooled, and quickly finely divided with scissors. Then, the solid content concentration was calculated by putting 5 g of the resultant hydrogel in a petri dish and then drying in a dryer of 180° C. for 24 hours. The solid content concentration of a particulate hydrogel was calculated by putting 5 g of a sample in a petri dish and then drying in a dryer of 180° C. for 24 hours.

[Calculation of Concentration Ratio]

The ratio (concentration ratio) is a ratio of a solid component concentration of a hydrogel as formed by polymerization to a solid component concentration in an aqueous solution of a monomer component. Herein, the solid component in the aqueous solution of the monomer component means a monomer and other additives, and does not include water and solvents. For example, when the solid component concentration in the aqueous solution of the monomer component is 40 weight %, and the solid component concentration of the hydrogel as formed is 48 weight %, the concentration ratio is calculated as follows: 48/40=1.20.

[Measurement of Absorption Capacity Under Load (AAP)]

An amount of 0.9 g of water-absorbent resin was uniformly spread on a stainless wire net of 400 mesh (mesh opening size: 38 μm) as attached by fusion to the bottom of a plastic supporting cylinder of an inner diameter 60 mm, on which a piston and a load were further mounted in sequence, wherein: the total weight was adjusted to 565 g so that a load of 20 g/cm$^2$ (corresponding to 1.96 kPa) could be uniformly applied to the water-absorbent resin, and the piston had an outer diameter only a little smaller than 60 mm and made no gap with the wall face of the supporting cylinder, but was not hindered from moving up and down. Then, the weight (Wa) of the resultant set of measurement apparatus was measured.

A glass filter having a diameter of 90 mm was mounted inside a Petri dish having a diameter of 150 mm, and a 0.9 weight % aqueous NaCl solution was added up to the same level as the upper surface of the glass filter, on which a filter paper having a diameter of 90 mm was then mounted such that its entire surface would be wet, and the excessive liquid was removed.

The above set of measurement apparatus was mounted on the above wet filter paper, thereby allowing to absorb the liquid under a load. After 1 hour, the set of measurement apparatus was lifted and removed, and its weight (Wb) was measured again.

The absorption capacity under a load (AAP) is calculated in accordance with the following equation:

$AAP(g/g)=(Wb-Wa)/0.9$

[Measurement of Temperature of Polymerization System]

For measuring the temperature of the system of which the temperature was rapidly changed, a deta-collecting system of PC card type NR-1000 (made by Keyence Co., Ltd.) was used, and the temperature was measured with a sampling cycle of 0.1 second by installing a thermocouple in the polymerization system. From the resultant temperature-time chart, the polymerization initiation temperature and the peak temperature (highest temperature) were read.

[Polymerization Time]

Measured was how long time passed since the aqueous solution of the monomer component was added to the polymerization vessel until the peak temperature. Specifically, the following was measured: (induction period)+(how long time passed since the initiation of the polymerization until the peak temperature was reached).

EXAMPLE 1

A mixed solution was continuously supplied into a continuous kneader (made by Dalton Co., Ltd., CKDJS-40) as a polymerization vessel having two agitation paddles, wherein the mixed solution was obtained by line-mixing the following components with amounts per minute: 493.2 g of acrylic acid, 396.1 g of 48 weight % aqueous sodium hydoxide solution, 419.6 g of water, 6.0 g of 0.5 weight % aqueous solution of diethylene triamine pentaacetic acid pentasodium salt, 1.0 g of polyethylene glycol diacrylate (average polyethylene glycol unit number: 8) as an internal-crosslinking agent, and 11.3 g of 3 weight % aqueous sodium persulfate solution. Incidentally, the concentration of the aqueous solution of the water-soluble unsaturated monomer component was 45 weight %, and the temperature of the mixed solution as supplied to the polymerization vessel reached 97° C. by the heat of neutralization and heat of dissolution. In addition, the jacket temperature of the above polymerization vessel was adjusted to 100° C., and nitrogen gas was blown into the polymerization vessel at a flow rate of 20 L/minute.

The polymerization was initiated as soon as the above mixed solution was supplied into the polymerization vessel, and the resultant crosslinked hydrogel polymer was sheared while the polymerization was carried out, and the resultant crushed hydrogel (1) was continuously discharged from the polymerization vessel. In addition, the peak temperature of the reaction system was then 101.2° C.

The hydrogel (1) as obtained in this way was spread on a metal gauze with a mesh opening size of 850 μm to form a layer of about 50 mm in thickness. Subsequently, the hydrogel was hot-wind-dried by passing a hot wind having a temperature of 170° C. (dew point: 50° C.) at a speed of 1 m/sec through the hydrogel in its vertical direction for 40 minutes. Pulverized was a block-shaped dried material which was obtained in this way and comprised of a particulate dry polymer, and further the resultant pulverized product was classified with a JIS standard sieve having a mesh opening size of 850 μm, thus obtaining a water-absorbent resin powder (1).

The results are listed in Table 1.

EXAMPLE 2

A water-absorbent resin powder (2) was obtained in the same way as of Example 1 except for being changed as follows: 435.7 g of acrylic acid, 349.9 g of 48 weight % aqueous sodium hydoxide solution, 193.3 g of water, 5.3 g of 0.5 weight % aqueous solution of diethylene triamine pentaacetic acid pentasodium salt, 0.44 g of polyethylene glycol diacrylate (average polyethylene glycol unit number: 8) as an internal-crosslinking agent, and 10.1 g of 3 weight % aqueous sodium persulfate solution. Incidentally, the concentration of the aqueous solution of the water-soluble unsaturated monomer component was then 53 weight %, and the temperature of the above aqueous solution as supplied to the polymerization vessel was 99° C., and the peak temperature of the reaction system was 102.1° C.

The results are listed in Table 1.

EXAMPLE 3

A water-absorbent resin powder (3) was obtained in the same way as of Example 1 except for being changed as follows: 438.4 g of acrylic acid, 352.1 g of 48 weight % aqueous sodium hydoxide solution, 520.5 g of water, 5.3 g of 0.5 weight % aqueous solution of diethylene triamine pentaacetic acid pentasodium salt, 1.48 g of polyethylene glycol diacrylate (average polyethylene glycol unit number: 8) as an internal-crosslinking agent, and 10.1 g of 3 weight % aqueous sodium persulfate solution. Incidentally, the concentration of the aqueous solution of the water-soluble unsaturated monomer component was then 40 weight %, and the temperature of the above aqueous solution as supplied to the polymerization vessel was 92° C., and the peak temperature of the reaction system was 100.5° C.

The results are listed in Table 1.

EXAMPLE 4

A water-absorbent resin powder (4) was obtained in the same way as of Example 1 except that: 0.053 g per minute of 2-hydroxy-2-methyl-1-phenyl-propane-1-one was added to the aqueous solution of the water-soluble unsaturated monomer component as line-mixed, and further a blacklight mercury lamp (peak wave length: 352 nm, form: H400BL; as provided in. a searchlight projector (MT4020); and both made by Toshiba Lighting & Technology Corporation) was set on a ceiling plate of the continuous kneader, and the UV-radiation was carried out. Incidentally, the temperature of the aqueous solution of the water-soluble unsaturated monomer component as supplied to the polymerization vessel was then 97° C., and the peak temperature of the reaction system was 102.0° C.

The results are listed in Table 1.

EXAMPLE 5

A water-absorbent resin powder (5) was obtained in the same way as of Example 1 except that: the water-absorbent resin powder (1) as obtained in Example 1 was classified with a JIS standard sieve having a mesh opening size of 150 μm, and 60 g per minute of the resultant fine powder was continuously supplied into the polymerization vessel. Incidentally, the peak temperature of the reaction system was 101.8° C.

The results are listed in Table 1.

EXAMPLE 6

Prepared was an aqueous solution of a water-soluble unsaturated monomer component, including 162.7 g of acrylic acid, 1,722.3 g of 37 weight % aqueous sodium acrylate solution, and 1.75 g of polyethylene glycol diacrylate (average polyethylene glycol unit number: 8) as an internal-crosslinking agent. Subsequently, the replacement with nitrogen was carried out for the above aqueous solution of the monomer component for 30 minutes. Thereafter, 90.3 g of 1 weight % aqueous sodium persulfate solution and 22.6 g of 0.2 weight % aqueous L-ascorbic acid solution were added to the above aqueous solution of the monomer component, and at the same time the resultant mixture was warmed through a SUS tube immersed in an oil bath of 65° C., and then the mixture was supplied into a polymerization vessel causing shearing action. Incidentally, a jacketed stainless twin-arm kneader of 10 liters in capacity with two sigma-type blades was used as the above polymerization vessel, and the jacket temperature of the polymerization vessel was raised to 95° C. by passing warm water, and the above aqueous solution was supplied while the blades were rotated. Incidentally, the concentration of the aqueous solution of the monomer component was then 40 weight %. The polymerization was initiated after 10 seconds from the supply of the above aqueous solution, and the resultant crosslinked hydrogel polymer was sheared while the polymerization was carried out. After 1 minute, the reaction system reached its peak temperature of 102° C., and then the polymerization was completed after 10 minutes since the peak temperature was shown.

A hydrogel (6) as obtained in this way was dried, pulverized, and classified in the same way as of Example 1, thus obtaining a water-absorbent resin powder (6).

The results are listed in Table 1.

EXAMPLE 7

Prepared was an aqueous solution of a water-soluble unsaturated monomer component, including 162.7 g of acrylic acid, 1,722.3 g of 37 weight % aqueous sodium acrylate solution, and 1.75 g of polyethylene glycol diacrylate (average polyethylene glycol unit number: 8) as an internal-crosslinking agent. Subsequently, the replacement with nitrogen was carried out for the above aqueous solution of the monomer component for 30 minutes. Thereafter, 90.3 g of 1 weight % aqueous sodium persulfate solution and 22.6 g of 0.2 weight % aqueous L-ascorbic acid solution were added to the above aqueous solution of the monomer component, and at the same time the resultant mixture was warmed through a SUS tube immersed in an oil bath of 55° C., and then the mixture was supplied into a polymerization vessel causing the same (condition of) shearing action as of Example 6. Incidentally, the concentration of the aqueous solution of the monomer component was then 40 weight %. The polymerization was initiated after 17 seconds from the supply of the above aqueous solution, and the resultant crosslinked hydrogel polymer was sheared while the polymerization was carried out. After 1.5 minutes, the reaction system reached its peak temperature of 103.5° C., and then the polymerization was completed after 10 minutes since the peak temperature was shown.

A hydrogel (7) as obtained in this way was dried, pulverized, and classified in the same way as of Example 1, thus obtaining a water-absorbent resin powder (7).

The results are listed in Table 1.

EXAMPLE 8

Prepared was an aqueous solution of a water-soluble unsaturated monomer component by blending: a solution as obtained by dissolving 0.42 g of polyethylene glycol diacrylate (average polyethylene glycol unit number: 8) as an internal-crosslinking agent into 618 g of acrylic acid; 495 g of 48.5 weight % aqueous sodium hydroxide solution; and 335 g of water, at a stroke. Subsequently, the replacement with nitrogen was carried out for the above aqueous solution of the monomer component for 30 minutes. Thereafter, 51.5 g of 0.5 weight % aqueous sodium persulfate solution was added to the above aqueous solution of the monomer component, and at the same time the resultant mixture was warmed through a SUS tube immersed in an oil bath of 96° C., and then the mixture was supplied into a polymerization vessel causing the same (condition of) shearing action as of Example 6. Incidentally, the aqueous solution of the monomer component then had a concentration of 50 weight %, and a neutralization ratio of 70 mol %. The polymerization was initiated after 5 seconds from the supply of the above aqueous solution, and the resultant crosslinked hydrogel polymer was sheared while the polymerization was carried out. After 1 minute, the reaction system reached its peak temperature of 102.8° C., and then the polymerization was completed after 3 minutes since the peak temperature was shown.

A hydrogel (8) as obtained in this way was pulverized with a vertical pulverizer (type: VM27-S, made by Orient Co., Ltd., diameter of screen: 8 mm) in order to obtain a particulate hydrogel, and the particulate hydrogel was spread on a metal gauze with a mesh opening size of 850 µm to form a layer of about 50 mm in thickness. Subsequently, the hydrogel was hot-wind-dried by passing a hot wind having a temperature of 170° C. (dew point: 50° C.) at a speed of 1 m/sec through the hydrogel in its vertical direction for 20 minutes. Pulverized was a block-shaped dried material which was obtained in this way and comprised of a particulate dry polymer, and further the resultant pulverized product was classified with a JIS standard sieve having a mesh opening size of 850 µm, thus obtaining a water-absorbent resin powder (8).

The results are listed in Table 1.

EXAMPLE 9

A water-absorbent resin powder (9) was obtained in the same way as of Example 8 except for using water obtained by cooling and recycling vapor in the polymerization vessel in Example 1 as the 335 g of water in the aqueous solution of the water-soluble unsaturated monomer component in Example 8. Incidentally, the peak temperature of the reaction system was then 103.3° C.

The results are listed in Table 1.

EXAMPLE 10

To 500 g of the water-absorbent resin powder (1) as obtained in Example 1, an aqueous surface-crosslinking agent solution including 1,4-butanediol, propylene glycol, and water in amounts of 0.32 weight %, 0.5 weight %, and 2.73 weight % (relative to the powder) respectively was added, and the resultant mixture was heated for 30 minutes in a mixer as heated in an oil bath of 212° C., thus obtaining a surface-crosslinked water-absorbent resin powder (10).

The result is listed in Table 2.

EXAMPLE 11

To 500 g of the water-absorbent resin powder (2) as obtained in Example 2, an aqueous surface-crosslinking agent solution including 1,4-butanediol, propylene glycol, and water in amounts of 0.32 weight %, 0.5 weight %, and 2.73 weight % (relative to the powder) respectively was added, and the resultant mixture was heated for 25 minutes in a mixer as heated in an oil bath of 212° C., thus obtaining a surface-crosslinked water-absorbent resin powder (11).

The result is listed in Table 2.

EXAMPLE 12

To 500 g of the water-absorbent resin powder (3) as obtained in Example 3, an aqueous surface-crosslinking agent solution including 1,4-butanediol, propylene glycol, and water in amounts of 0.32 weight %, 0.5 weight %, and 2.73 weight % (relative to the powder) respectively was added, and the resultant mixture was heated for 25 minutes in a mixer as heated in an oil bath of 212° C., thus obtaining a surface-crosslinked water-absorbent resin powder (12).

The result is listed in Table 2.

EXAMPLE 13

To 500 g of the water-absorbent resin powder (6) as obtained in Example 6, an aqueous surface-crosslinking agent solution including 1,4-butanediol, propylene glycol, and water in amounts of 0.32 weight %, 0.5 weight %, and 2.73 weight % (relative to the powder) respectively was added, and the resultant mixture was heat-stirred for 35 minutes in a mixer as heated in an oil bath of 212° C., thus obtaining a surface-crosslinked water-absorbent resin powder (13).

The result is listed in Table 2.

[Comparative Example 1]

Prepared was an aqueous solution of a water-soluble unsaturated monomer component with a concentration of 41 weight %, including 633.4 g of acrylic acid, 5550.6 g of 37 weight % aqueous sodium acrylate solution, 3.72 g of polyethylene glycol diacrylate (average polyethylene glycol unit number: 8) as an internal-crosslinking agent, and 342.4 g of water.

The above aqueous solution of the water-soluble unsaturated monomer component was supplied to the polymerization vessel of Example 1, and the atmosphere in the polymerization vessel was replaced with nitrogen for 30 minutes while the above aqueous solution was maintained at 25° C. Subsequently, while the jacket temperature of the polymerization vessel was adjusted to 25° C. under a stream of nitrogen and the blades were rotated, 24.5 g of 15 weight % aqueous sodium persulfate solution and 15.3 g of 0.2 weight % aqueous L-ascorbic acid solution were added thereto. As a result, the polymerization was initiated after 10 seconds. The warm water of the jacket was heated to 70° C. at the same time as the initiation of the polymerization, and the resultant crosslinked hydrogel polymer was sheared while the polymerization was carried out. After 6.5 minutes, the reaction system reached its peak temperature, and then the polymerization was completed after 20 minutes since the peak temperature was shown.

A comparative hydrogel (1) as obtained in this way was spread on a metal gauze with a mesh opening size of 850 μm to form a layer of about 50 mm in thickness. Subsequently, the hydrogel was hot-wind-dried by passing a hot wind having a temperature of 170° C. (dew point: 50° C.) at a speed of 1 m/sec through the hydrogel in its vertical direction for 60 minutes. Pulverized was a block-shaped dried material which was obtained in this way and comprised of a particulate dry polymer, and further the resultant pulverized product was classified with a JIS standard sieve having a mesh opening size of 850 μm, thus obtaining a comparative water-absorbent resin powder (1).

The results are listed in Table 1.

[Comparative Example 2]

A comparative water-absorbent resin powder (2) was obtained in the same way as of Comparative Example 1 except for being changed as follows: 908.5 g of acrylic acid, 4,807.1 g of 37 weight % aqueous sodium acrylate solution, 3.83 g of polyethylene glycol diacrylate (average polyethylene glycol unit number: 8) as an internal-crosslinking agent, 809.6 g of water, 25.2 g of 15 weight % aqueous sodium persulfate solution, and 15.8 g of 0.2 weight % aqueous L-ascorbic acid solution.

The results are listed in Table 1.

[Comparative Example 3]

Prepared was an aqueous solution of a water-soluble unsaturated monomer component with a concentration of 41 weight %, including 192.8 g of acrylic acid, 1689.7 g of 37 weight % aqueous sodium acrylate solution, 1.14 g of polyethylene glycol diacrylate (average polyethylene glycol unit number: 8) as an internal-crosslinking agent, and 104.2 g of water.

The replacement with nitrogen was carried out for the above aqueous solution of the water-soluble unsaturated monomer component for 30 minutes, and the aqueous solution was supplied to the polymerization vessel of Example 5, and the jacket temperature was adjusted to 50° C., and then the above aqueous solution of the water-soluble unsaturated monomer component was warmed to 50° C. Subsequently, while the blades were rotated under a stream of nitrogen, 7.5 g of 15 weight % aqueous sodium persulfate solution and 4.7 g of 0.2 weight % aqueous L-ascorbic acid solution were added thereto. As a result, the polymerization was initiated after 15 seconds. The warm water of the jacket was heated to 70° C. at the same time as the initiation of the polymerization, and the resultant crosslinked hydrogel polymer was sheared while the polymerization was carried out. After 1.5 minutes, the reaction system reached its peak temperature, and then the polymerization was completed after 10 minutes since the peak temperature was shown.

A comparative hydrogel (3) as obtained in this way was hot-wind-dried in the same way as of Example 1. Pulverized was a block-shaped dried material which was obtained in this way and comprised of a particulate dry polymer, and further the resultant pulverized product was classified with a JIS standard sieve having a mesh opening size of 850 μm, thus obtaining a comparative water-absorbent resin powder (3).

The results are listed in Table 1.

[Comparative Example 4]

To 500 g of the comparative water-absorbent resin powder (1) as obtained in Comparative Example 1, an aqueous surface-crosslinking agent solution including 1,4-butanediol, propylene glycol, and water in amounts of 0.32 weight %, 0.5 weight %, and 2.73 weight % (relative to the powder) respectively was added, and the resultant mixture was heated for 45 minutes in a mixer as heated in an oil bath of 212° C., thus obtaining a comparative surface-crosslinked water-absorbent resin powder (4).

The result is listed in Table 2.

[Comparative Example 5]

To 500 g of the comparative water-absorbent resin powder (2) as obtained in Comparative Example 2, an aqueous surface-crosslinking agent solution including 1,4-butanediol, propylene glycol, and water in amounts of 0.32 weight %, 0.5 weight %, and 2.73 weight % (relative to the powder) respectively was added, and the resultant mixture was heated for 30 minutes in a mixer as heated in an oil bath of 212° C., thus obtaining a comparative surface-crosslinked water-absorbent resin powder (5).

The result is listed in Table 2.

TABLE 1

| | GV (g/g) | Extractable content (weight %) | Amount of residual monomer (weight ppm) | Concentration of aqueous monomer solution (weight %) | Solid component concentration of hydrogel (weight %) | Neutralization ratio of hydrogel (%) | Concentration ratio | Solid component concentration of particulate hydrogel (weight %) | Increase of solid component concentration of hydrogel during disintegration (weight %) |
|---|---|---|---|---|---|---|---|---|---|
| Water-absorbent resin powder (1) | 39.0 | 12.0 | 840 | 45 | 57.5 | — | 1.278 | — | — |
| Water-absorbent resin powder (2) | 42.8 | 16.6 | 570 | 53 | 66.3 | — | 1.251 | — | — |
| Water-absorbent resin powder (3) | 44.1 | 10.3 | 980 | 40 | 51.2 | — | 1.280 | — | — |

TABLE 1-continued

|  | GV (g/g) | Extractable content (weight %) | Amount of residual monomer (weight ppm) | Concentration of aqueous monomer solution (weight %) | Solid component concentration of hydrogel (weight %) | Neutralization ratio of hydrogel (%) | Concentration ratio | Solid component concentration of particulate hydrogel (weight %) | Increase of solid component concentration of hydrogel during disintegration (weight %) |
|---|---|---|---|---|---|---|---|---|---|
| Water-absorbent resin powder (4) | 38.7 | 9.9 | 310 | 45 | 58.2 | — | 1.293 | — | — |
| Water-absorbent resin powder (5) | 38.1 | 13.2 | 920 | 45 | 61.3 | — | — | — | — |
| Water-absorbent resin powder (6) | 44.5 | 14.6 | 820 | 40 | 46.6 | — | 1.165 | — | — |
| Water-absorbent resin powder (7) | 47.5 | 14.5 | 380 | 40 | 45.9 | — | 1.148 | — | — |
| Water-absorbent resin powder (8) | 49.6 | 18.2 | 730 | 50 | 62.3 | 74.6 | 1.246 | 64.9 | 2.6 |
| Water-absorbent resin powder (9) | 49.1 | 17.7 | 760 | 50 | 61.7 | — | 1.234 | — | — |
| Comparative water-absorbent resin powder (1) | 45.9 | 20.6 | 310 | 41 | 42.7 | — | 1.041 | — | — |
| Comparative water-absorbent resin powder (2) | 47.7 | 26.5 | 110 | 41 | 41.9 | — | 1.022 | — | — |
| Comparative water-absorbent resin powder (3) | 48.9 | 24.5 | 580 | 41 | 44.8 | — | 1.093 | — | — |

As being understood from the results of Table 1, a water-absorbent resin (base polymer) was obtained with high productivity by carrying out the present invention, wherein the water-absorbent resin displayed high absorption capacity without load (GV) and had a small extractable content.

TABLE 2

|  | AAP (g/g) |
|---|---|
| Water-absorbent resin powder (10) | 31.3 |
| Water-absorbent resin powder (11) | 34.1 |
| Water-absorbent resin powder (12) | 34.8 |
| Water-absorbent resin powder (13) | 35.0 |
| Comparative water-absorbent resin powder (4) | 32.5 |
| Comparative water-absorbent resin powder (5) | 28.8 |

As being understood from the results of Table 2, a water-absorbent resin that displayed high absorption capacity under a load (AAP) could be obtained also among the surface-crosslinking-treated water-absorbent resins.

Industrial Application

The present invention can provide: a base polymer, which displays high absorption capacity without load and has a small extractable content; and a water-absorbent resin, which is surface-crosslinking-treated and displays high absorption capacity under a load, by reasonable steps.

The above effects are obtained, and therefore the water-absorbent resin as obtained by the present invention is useful for such as: uses contacting with human bodies, (e.g. sanitary articles, such as disposable diapers for child and adult, sanitary napkins, and incontinent articles for adult); water-retaining agents for plant or soil, water-holding materials for electric wire or photocable; and water-holding materials in engineering and construction works fields.

What is claimed is:

1. A production process for a water-absorbent resin, which comprises a polymerization step that includes the steps of: supplying an aqueous solution of a water-soluble unsaturated monomer component including a major proportion of acrylic acid and/or its salt into a polymerization vessel causing shearing action; and then carrying out polymerization, involving crosslinking, of the water-soluble unsaturated monomer and at the same time carrying out fine division of the resultant hydrogel,
    with the production process being characterized in that the aqueous solution of the water-soluble unsaturated monomer component as supplied into the polymerization vessel has a temperature of not lower than 40° C.

2. A production process according to claim 1, wherein the polymerization as carried out in the polymerization step is continuous polymerization that involves continuously supplying the aqueous solution of the water-soluble unsaturated monomer component and continuously discharging the resultant hydrogel.

3. A production process according to claim 1, wherein the water-soluble unsaturated monomer component in the aqueous solution has a concentration of not less than 30 weight %.

4. A production process according to claim 1, which involves a concentration ratio of not less than 1.10 wherein the concentration ratio is defined as a ratio of a solid component concentration of the resultant hydrogel as discharged from the polymerization vessel to a solid component concentration of the aqueous solution of the water-soluble unsaturated monomer component as supplied into the polymerization vessel.

5. A production process according to claim 1, wherein the hydrogel displays the highest temperature of not lower than 100° C. in the polymerization vessel.

6. A production process according to claim 1, which involves utilization of heat of neutralization and/or heat of dissolution of acrylic acid and an alkali for heating to raise the temperature of the aqueous solution of the water-soluble unsaturated monomer component as supplied into the polymerization vessel.

7. A production process according to claim 1, which further comprises the steps of collecting and then reusing acrylic acid and/or water having vaporized during the polymerization.

8. A production process according to claim 1, which involves a difference ΔT of not higher than 70° C. between the temperature of the aqueous solution of the water-soluble unsaturated monomer component as supplied into the polymerization vessel and the highest temperature of the hydrogel in the polymerization vessel.

9. A production process according to claim 1, which further comprises the step of adding a water-absorbent resin fine powder either to the aqueous solution of the water-soluble unsaturated monomer component as supplied into the polymerization vessel or at the same time as this supply of the aqueous solution of the water-soluble unsaturated monomer component.

10. A production process according to claim 1, wherein acrylic acid is used as the monomer in the water-soluble unsaturated monomer component and said component contains p-methoxyphenol.

11. A production process according to claim 1, which further comprises the step of carrying out disintegration of the resultant finely divided hydrogel, as discharged from the polymerization vessel, with a disintegrator having a screen.

12. A production process according to claim 11, wherein the finely divided hydrogel as discharged from the polymerization vessel is disintegrated with the disintegrator in such a manner that the solid component concentration will increase by not less than 2 weight % during the disintegration.

13. A production process according to claim 1, which further comprises a surface-crosslinking step after the polymerization step.

14. A water-absorbent resin as obtained by the production process as recited in claim 1, which displays an absorption capacity of not less than 20 g/g under a load.

15. A sanitary article, which comprises the water-absorbent resin as recited in claim 14.

16. A production process according to claim 1, wherein said polymerization vessel includes at least two agitation shafts rotating in different directions for directing a reaction mixture toward a center of said polymerization vessel.

17. A production process according to claim 16, comprising rotating said agitation shafts at the same speed.

18. A production process according to claim 16, comprising rotating said agitation shafts at different speeds.

19. A production process according to claim 1, wherein said resultant hydrogel has a solid component concentration in the range of 50 wt % to 80 wt %.

20. A production process according to claim 1, wherein said aqueous solution of said water-soluble unsaturated monomer component is supplied to said polymerization vessel at a temperature sufficient to remove dissolved oxygen.

21. A production process according to claim 20, wherein said aqueous solution of said water-soluble unsaturated monomer component is at a temperature of not lower than 50° C.

* * * * *